(12) United States Patent
Høyer et al.

(10) Patent No.: US 6,605,742 B2
(45) Date of Patent: Aug. 12, 2003

(54) CYCLO AZAPHOSPHA HYDROCARBONS

(75) Inventors: Thomas Høyer, Charlottenlund (DK); Morten Dahl Sørensen, Hørsholm (DK)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 10/119,769

(22) Filed: Apr. 11, 2002

(65) Prior Publication Data

US 2002/0177706 A1 Nov. 28, 2002

Related U.S. Application Data

(60) Provisional application No. 60/282,896, filed on Apr. 11, 2001.

(51) Int. Cl.$^7$ ........................ C07C 259/04; C07C 9/553; A61K 31/19
(52) U.S. Cl. ........................ 562/621; 562/622; 562/444; 562/433; 560/45; 564/13; 514/79; 514/110; 514/538; 514/575; 514/561; 514/567
(58) Field of Search .................. 514/79, 110, 538, 514/575, 561, 567; 564/13; 560/45; 562/621, 622, 433, 444

(56) References Cited

PUBLICATIONS

Hetherington et al, Tetrahedron, 56, 2053–2060, 2000.*
O'Brien et al, J. Med. Chem., 43, 156–166, 2000.*
Huby et al, J. Chem., Soc. perkin. Trans I, 145–155, 1991.*

* cited by examiner

*Primary Examiner*—Shailendra Kumar
(74) *Attorney, Agent, or Firm*—Birch, Stewart, Kolasch & Birch, LLP

(57) ABSTRACT

Novel cyclo azaphospha hydrocarbons according to formula I

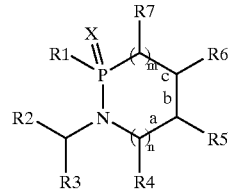

are provided. The compounds are useful as metalloprotease inhibitors.

9 Claims, No Drawings

CYCLO AZAPHOSPHA HYDROCARBONS

This application claims priority on provisional Application No. 60/282,896 filed on Apr. 11, 2001, the entire contents of which are hereby incorporated by reference.

FIELD OF THE INVENTION

The invention relates to a hitherto unknown class of compounds, namely cyclo azaphospha hydrocarbons, which exhibits matrix metalloprotease inhibitory effects, to pharmaceutical compositions comprising said compounds and to the use of said compounds in the manufacture of medicaments.

BACKGROUND OF THE INVENTION

The matrix metalloproteases (MMP) are a family of zinc containing enzymes capable of breaking down many proteinaceous compounds in the extracellular matrix, such as collagen, gelatine, fibronectin, laminin and proteoglucan core protein.

There are at least 23 different MMPs classified according to their domain structure and substrate preferences [Lauer-Fields, *Exp. Opin. Ther. Patents*, 10, 1873–1884, 2000]. MMP may be classified into four main groups: Collagenases degrade fibrilar collagen; stromelysin degrade proteoglucans and glucoproteins; gelatinases degrade non-fibrilar and degraded collagen, i.e. gelatine; and finally the membrane bound MMPs [O'Brien, *J. Med. Chem.*, 43, 156–166, 2000]. The MMPs share a common multidomain structure, but are glycosylated at different sites and to different extent. All MMPs also share a common zinc-binding motif, HisGluXaaGlyHis, and the differences comprise the presence or absence of structural domains controlling such factors as substrate specificity, inhibitor binding, matrix binding and cell-surface localisation. The nomenclature for MMP is simple as they are named MMP-n, wherein n is an integer starting from 1.

MMP plays an important physiological role in tissue remodelling in normal tissue, e.g. angiogenesis, wound healing, bone resorption, ovulation and embryonic development. In healthy tissue, the activity of MMP is carefully controlled by gene expression, by synthesis of the enzymes in a latent pro-enzyme form, and by co-expression of endogenous tissue inhibitors of MMP (TIMP). Excessive or poorly regulated MMP activity has been implicated in a host of pathological conditions, and there has thus been a large effort to design drugs with MMP inhibitor effects, which could be used to re-establish control of the MMP activity.

Many known MMP inhibitors are peptide derivatives, based on naturally occurring amino acids, and with structural similarities to the cleavage sites in the natural substrates of MMP. Other known MMP inhibitors have less peptidic structure, and may be classified as pseudopeptides or peptidomimetics, e.g. sulfonamides.

Prior art of MMP inhibitors consists of peptidic structures [WO 95/19965 and WO 95/19956]; linear and cyclic sulfonamide compounds, [WO 97/44315, WO 00/09485 and EP 0979 816] and buturic and pentanoic acid derivatives [WO 97/43237, WO 97/43239 and WO 99/61413].

SUMMARY OF THE INVENTION

It has surprisingly been found that the novel cyclo azaphospha hydrocarbon derivatives of general formula I are potent inhibitors of MMP.

Accordingly, the present invention relates to a compound of general formula I

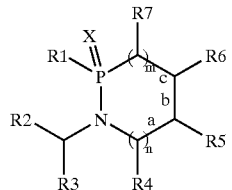

[I]

wherein bonds denoted a, b and c independently represents single or double bonds;
m and n are independently 0, 1, 2 or 3, provided that m and n are not both 0;
X is S or O;
$R_1$ is

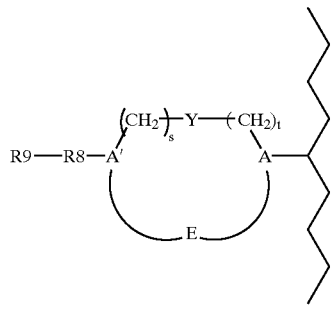

wherein E, when present represents a bond, methylene or ethylene optionally substituted with halogen, hydroxy, cyano, nitro, $C_{1-4}$ alkyl, haloalkyl, hydroxyalkyl, alkoxy or alkylcarbonyl;
s and t are independently 0, 1, 2 or 3;
A and A' independently represent a bond, or a saturated or unsaturated, optionally substituted cyclic or heterocyclic hydrocarbon di- or triradical;
Y represents a bond, O, S, C(O)$NR_{10}$, $NR_{10}$C(O) or $NR_{10}$, wherein $R_{10}$ is hydrogen, hydroxy, branched or straight, saturated or unsaturated hydrocarbon radical, optionally substituted with halogen, nitro, cyano, hydroxyl, alkoxy, alkylcarbonyl or alkylamino;
$R_8$ represents a bond, hydrogen, alkanediyl or alkendiyl diradical, one or more ether diradicals (R'—O—R") or amine diradicals (R'—N—R"), wherein R' and R" independently represent alkyl or alkenyl with a C-content from 0 to 3;
$R_9$ represents hydrogen, hydroxy, halogen, cyano, nitro, branched or straight, saturated or unsaturated hydrocarbon radical, optionally substituted with halogen, cyano, hydroxyl, alkoxy, alkylcarbonyl or alkylamino; $NR_{11}R_{12}$, C(O)$NR_{11}R_{12}$, C(O)$R_{11}R_{12}$, CO(O)$R_{11}R_{12}$, S(O)$_2R_{11}$, wherein each $R_{11}$ and $R_{12}$ independently represent hydrogen, halogen, a branched or straight, saturated or unsaturated hydrocarbon radical, optionally substituted with halogen, cyano, hydroxyl, alkoxy, alkylcarbonyl or alkylamino;
$R_2$ represents hydroxamic acid, carboxylic acid, phosphonic acid or a mercaptomethyl group;
$R_3$ and $R_4$ each independently represent hydrogen, halogen, cyano, hydroxy, nitro, branched or straight, saturated or unsaturated hydrocarbon radical, optionally substituted with halogen, cyano, nitro, hydroxy; alkoxy, hydroxy, alkylcarbonyl, alkylamino; or $R_3$ and $R_4$ together with the carbon atoms to which they are attached and the connecting nitrogen atom form a heterocyclic ring; each $R_5$, $R_6$, and $R_7$ independently represents hydrogen, hydroxy, nitro, cyano, halogen, branched or straight, saturated or unsaturated hydrocarbon radical, optionally substituted with halogen, cyano, nitro, hydroxyl, alkoxy, alkylcarbonyl or alkylamino; or $R_4$ and $R_5$, $R_5$ and $R_6$ or $R_6$ and $R_7$, together with the carbon atom to which they are attached form a saturated or unsaturated, optionally substituted cyclic or heterocyclic ring;

and pharmaceutically acceptable salts thereof.

In another aspect, the invention relates to a pharmaceutical composition comprising a compound of formula I, together with a pharmaceutically acceptable excipient.

In still another aspect, the invention relates to a method of treating or preventing diseases or conditions involving tissue breakdown, inflammation or proliferative disorder comprising administering to a patient in need thereof an effective amount of a compound of formula I.

In a still further aspect, the invention relates to the use of a compound of formula I for the manufacture of a medicament for the treatment or profylaxis of diseases or conditions involving tissue breakdown, inflammation or proliferative disorder.

DETAILED DESCRIPTION OF THE INVENTION

The term "halogen" when used herein is intended to indicate members of the seventh main group of the periodic table, i.e. flouro, chloro, bromo and iodo.

The term "alkane" is intended to indicate straight, branched or cyclic compounds, containing carbon and hydrogen, which are saturated. The term includes the subclasses primary, secondary and tertiary alkane, such as methane, ethane, n-propane, iso-butan, tert. butan, cyclohexan, cyclopentan.

The term "alkene" is intended to indicate straight, branched or cyclic compounds, containing carbon and hydrogen, and with at least one double bond. The term includes primary secondary and tertiary alkene, such as ethene, propene, 1-butene, 2-butene, 3,3-dimethyl-1-butene, cyclopropene, cyclohexen e.

The term "alkyl" is intended to indicate a univalent radical derived from straight, branched or cyclic alkane by removing a hydrogen atom from any carbon atom. The term includes the subclasses primary, secondary and tertiary alkyl, such as methyl, ethyl, n-propyl, isopropyl, n-butyl, isobutyl, tert.-butyl, isopentyl, isohexyl, cycloheptyl, cyclohexyl, cyclopentyl and cyclopropyl.

The term "haloalkyl" is intended to indicate partially or fully halogenated alkyl radicals, such as trifluoromethyl.

The term "hydroxyalkyl" is intended to indicate an alkyl substituted with one or more hydroxy groups, such as 2-hydroxyethyl, 2-hydroxypropyl and 2,4-dihydroxypentyl.

The term "alkoxy" is intended to indicate a radical of formula OR', wherein R' is alkyl as defined above, e.g. methoxy, ethoxy, propoxy, butoxy, etc.

The term "alkoxycarbonyl" is intended to indicate a radical of formula —COOR' wherein R' is alkyl as defined above, e.g. methoxycarbonyl, ethoxycabonyl, n-propoxycarbonyl, isopropoxycarbonyl, etc.

The term "saturated cyclic hydrocarbon" is intended to indicate cyclic compounds, optionally fused bicyclic rings, containing hydrogen and carbon, which are saturated, such as cyclopropane, cyclobutane, cyclopentane, cyclohexane, cycloheptane, cyclooctane, hydrindane and decaline.

The term "unsaturated cyclic hydrocarbon" is intended to indicate cyclic compounds, optionally fused bicyclic rings, containing hydrogen and carbon, in which one or more carbon—carbon bond is unsaturated, such as cyclopentene, cyclohexene, cyclohexadiene, cycloheptene, benzene, naphtene and 1,4-dihydronaphtene, indane and indene.

The term "heterocyclic hydrocarbon" is intended to indicate saturated or unsaturated cyclic compounds of hydrogen, carbon, and one or more heteroatoms selected from O, S and N, such as pyrrole, furan, thiophene, imidazole, oxazole, thiazole, pyrazole, pyrrolidine, pyridine, pyrimidine, tetrahydrotiophene, tetrahydrofuran, piperidine, piperazine, phosphalane, phosphorinane and phosporepane.

The terms "monoradical", "diradical" and "triradical" is intended to indicate a moity from which one, two or three hydrogens, respectively, have been removed.

The term "pharmaceutically acceptable salt" is intended to indicate salts prepared by reacting a compound of formula I with a suitable inorganic or organic acid, e.g. hydrochloric, hydrobromic, hydroiodic, sulfuric, nitric, acetic, phosphoric, lactic, maleic, phthalic, citric, propionic, benzoic, glutaric, gluconic, methanesulfonic, salicylic, succinic, tartaric, toluenesulfonic, sulfamic or fumaric acid. Pharmaceutically acceptable salts of compounds of formula I may be prepared by reaction with a suitable base such as sodium hydroxide, potassium hydroxide, ammonia, amines or the like.

The term "effective amount" is intended to indicate the amount which is required to confer a therapeutic effect to the treated patient, and is typically determined on the basis of the route of administration; age, body weight, sex, health and condition of the patient; the nature and extend of the symptoms; the kind of concurrent treatment; the frequency of treatment; and the desired effect.

The term "excipient" is intended to indicate all substances in a pharmaceutical formulation which are not active ingredients, such as e.g. carriers, binders, lubricants, thickeners, surface active agents, preservatives, emulsifiers, buffers, flavouring agents or colorants.

The pharmacophore of many MMP inhibitors reported in the literature comprises two elements vital to their function: 1) A zinc binding group, often hydroxamic acid, reverse hydroxamic acid, oxygenated phosphorous groups (e.g. phosphinic acid and phosphonamides including aminophosphonic acid) carboxylic acid, or mercaptomethyl which ligates to the zinc in the active site of the MMP; and 2) groups which can interact with specific subsites near to the active site of MMP [O'Bien, *J. Med. Chem,* 43, 156–166, 2000; Hajduk, *J. Am. Chem. Soc,* 119, 5818–5827, 1997]. It is well known that different MMP inhibitors exhibit different selectivity towards the known MMPs. From X-ray analyses of MMPs it emerge that MMPs may be classified into two large subgroups according to the depth of the S1' subsite or pocket, i.e. either as deep or short S1' pocket enzymes. The S1' pocket is also referred to as the "selectivity pocket" because the size of the inhibitor moiety interacting with the S1' pocket, appears to determine the specificity of the inhibitor [Whitaker, *Chem. Rev*, 99, 2735–2776, 1999]. It is found that large substituents on the inhibitor next to the zinc-binding group enhances inhibitory activity towards deep pocket MMPs, such as MMP-2, MMP-9 and MMP-3, at the expense of short pocket MMPs, such as MMP-1 and MMP-7. However, as all MMPs share a common active site, all MMPs are to some extend inhibited by any MMP inhibitor, and no true selectivity for a single MMP has been achieved [Brown, *Exp. Opin. Invest. Drugs*, 9, 2167–2177, 2000].

Many highly potent MMP inhibitors have been developed with $IC_{50}$ in the nanomolar range when tested in vitro. Unfortunately, these compounds show poor bioavailability, and they have thus little use in therapeutic treatments [Brown, *Breast Cancer Res. Treat.*, 52, 125–136, 1998]. Hence, it is still a challenge to develop compounds with the right balance between MMP inhibition, water solubility, oral avilability, pharmacokinetic characteristics, etc required for useful in vivo MMP inhibitors.

It has now surprisingly been found that a novel type of compounds, i.e. cyclo azaphospha hydrocarbons of the general formula I exhibit high MMP inhibitory activity.

In a preferred embodiment, X is O.

In a further preferred embodiment, a and c are both single bonds; b is a double bond; and $R_4$ and $R_7$ are independently either hydrogen or methyl.

In a still further preferred embodiment, E is absent; s and t are both 0; Y is O in the para position on A; A being phenyl.

In a still further preferred embodiment, $R_2$ is hydroxamic acid.

In a still further preferred embodiment, the compound of formula I is selected from the group consisting of
(±)-N-hydroxy-2-oxo-2-(4-phenoxyphenyl)-azaphosphorin-4-ene-1-acetamide;
(±)-N-hydroxy-2-oxo-2-(4-phenoxyphenyl)-azaphosphorinane-1-acetamide;
(±)-N-hydroxy-2-oxo-2-(4-phenyl-azaphosphorep-5-ene-1-acetamide;
(±)-N-hydroxy-2-oxo-2-(4-phenoxyphenyl)-azaphosphorepane-1-acetamide;
(±)-N-hydroxy-2-(4-(4-chlorophenoxy)-phenyl-2-oxo-azaphosphorin-4-ene-1-acetamide;
(±)-N-hydroxy-2-(4-Methoxyphenyl)-2-oxo-azaphosphorolane-1-acetamide;
(±)-(R*,R*,S*)-N-hydroxy-2-oxo-2-(4-phenoxyphenyl)-1,2-azaphosphabicyclo[4.3.0]non-4-ene-9-carboxamide;
(±)-N-hydroxy-2-(4-Ethoxyphenyl)-2-oxo-azaphosphoroc-6-ene-1-acetamide;
(±)-N-hydroxy-2-(4-Ethoxyphenyl)-2-oxo-azaphosphorin-4-ene-1-acetamide;
(±)-2-(4-Ethoxyphenyl)-2-oxo-azaphosphorin-4-ene-1-acetic acid;
(±)-N-hydroxy-2-(4-Ethoxyphenyl)-2-oxo-azaphosphorinane-1-acetamide;
(±)-N-hydroxy-2-(4-Ethoxyphenyl)-2-oxo-azaphosphorocane-1-acetamide;
(±)-2-(4-Ethoxyphenyl)-2-oxo-azaphosphorep-5-ene-1-acetic acid;
(±)-N-hydroxy-2-(4-(2-methylpropoxy)-phenyl)-2-oxo-azaphosphorin-4-ene-1-acetamide;
(±)-N-hydroxy-2-(4-Ethoxyphenyl)-2-oxo-azaphosphorepane-1-acetamide; and
(±)-N-hydroxy-2-(4-(2-methylpropoxy)-phenyl)-2-oxo-azaphosphorinane-1-acetamide.

Compounds of the general formula I contain asymmetric carbon atoms as well as carbon—carbon double bonds, which allow for isomeric forms. It will be appreciated that the present invention relates to any tautomeric, diastereomeric or optical isomeric form, either in pure form or as mixtures thereof, represented by the formula I.

Imbalance in MMP production or activity has been implicated in many diseases, hence the therapeutic value of MMP inhibitors. Compounds that have the property of inhibiting MMP are thus believed to be potentially useful for treating, preventing and/or ameliorating disease severity, disease symptoms, and/or periodicity of reoccurrence of a disease or condition associated with an imbalance in MMP production or activity. Diseases or conditions include, but are not limited to those involving tissue breakdown or inflammation, such as rheumatoid arthritis, osteoarthritis, osteopenias, such as osteroporosis, periodontitis, gingivitis, corneal epidermal or gastric ulceration, skin aging, tumour metastasis, tumour invasion and tumour growth; diseases associated with neuroinflammatory disorder, including those involving myelin degradation, such as multiple sclerosis; angiogenesis dependent diseases, which include arthritic conditions and solid tumour growth, psoriasis, proliferative retinopathies, neovascular glaucoma, ocular tumours, angiofibromas and hemangiomas [Vu in *Metalloproteases*, Parks and Mecham (Eds.), 115–148, 1998, Academic Press; Mullins, *Biochem. Biophys. Acta*, 695, 117–214, 1983; Henderson, *Drugs of the Future*, 15, 495–508, 1990; Reich, *Cancer Res*, 48, 3307–3312, 1988; Whitaker, *Chem. Rev.*, 99, 2735–2776, 1999].

Moreover, MMP inhibitors are also potentially useful for treating, preventing and/or ameliorating disease severity, disease symptoms, and/or periodicity of reoccurrence of a disease or condition associated excess Tumour Necrosis Factor α (TNF-α) production [Whitaker, *Chem. Rev.*, 99, 2735–2776, 1999]. TNF-α is a potent proinflammatory cytokine which has been implicated in inflammatory diseases or conditions, arthritis, asthma, septic shock, fever, cardiovascular effects, haemorrage, coagulation, acute phase reponse and apoptosis. TNF-α is expressed in the cells as a membrane-bound 26 kDa protein, which is proteolytically cleaved to release a 17 kDa active, soluble form. The TNF-α processing is catalysed by the enzyme TNF-α convertase (TACE), which is a metalloprotease, and several MMP inhibitors have been found to inhibit TNF-α processing [Mohler, *Nature*, 370, 218, 1994]. Excess TNF-α production can thus potentially be controlled by treatment with an MMP inhibitor.

In another aspect, the invention relates to a pharmaceutical formulation of a compound of formula I. The formulations of the present invention, both for veterinary and for human medical use, comprise active ingredients in association with a pharmaceutically acceptable carrier(s) and optionally other therapeutic ingredient(s). The carrier(s) must be "acceptable" in the sense of being compatible with the other ingredients of the formulations and not deleterious to the recipient thereof.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations may conveniently be presented in dosage unit form and may be prepared by any of the methods well known in the art of pharmacy, e.g as disclosed in Remington, *The Science and Practise of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methyl cellulose, agar, bentonite, xanthan gum or the like or dispersing agent. Moulded tablets may be made by moulding, in a suitable machine, a mixture of the powdered active ingredient and suitable carrier moistened with an inert liquid diluent.

Formulations for rectal administration, e.g. injection or infusion, may be in the form of a suppository incorporating the active ingredients and a carrier, or in the form of an enema.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. U.S. Pat. Nos. 5,534,499, 5,762,958 and 6,007,839 are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers.

In addition to the formulations described previously, the compound of formula I may also be presented as a depot preparation. Such long acting formulations may be administered by implantation (e.g. subcutaneously or intramuscular) or by intramuscular injection. Thus, for example, the compound of formula I may be formulated with suitable polymeric or hydrophobic materials (e.g. as an emulsion in an acceptable oil), with ion exchange resin, or with sparingly soluble derivatives, for example as a sparingly soluble salt.

In the systemic treatment using the present invention daily doses of from 0.001–200 mg per kilogram body weight, preferably from 0.002–50 mg/kg of mammal body weight, for example 0.003–20 mg/kg of a compound of formula I is administered, typically corresponding to a daily dose for an adult human of from 0.2 to 750 mg. In the topical treatment of dermatological disorders, ointments, creams or lotions containing from 0.1–750 mg/g, and preferably from 0.1–500 mg/g, for example 0.1 200 mg/g of a compound of formula I is administered. For topical use in ophthalmology ointments, drops or gels containing from 0.1–750 mg/g, and preferably from 0.1–500 mg/g, for example 0.1–200 mg/g of a compound of formula I is administered. The oral compositions are formulated, preferably as tablets, capsules, or drops, containing from 0.05–250 mg, preferably from 0.1–125 mg, of a compound of formula I per dosage unit.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including antioxidants), emulsifying agents and the like.

The invention also includes incorporating other pharmaceutically active ingredients, normally used in the treatment, into the formulation of the present invention. Without limitations, such other pharmaceutically active ingredients may be anti-cancer drugs, such as chemotherapeutic agents, hormonal agents, or biological response modifiers.

A crucial step in the synthesis of compounds of formula II, a subclass of compounds of formula I,

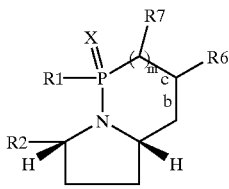

II wherein R1, R2, R6, R7, X, b, c and m are as described above, is the Ag+ catalysed stereoselective (the substituents on the pyrrolidine ring are positioned cis) cyclization of aminophospha allenes, as described in scheme 7, step 2. Huby, *J. Chem. Soc, Perkin Trans.*, 1, 145–155, 1991 discloses an Ag+ catalysed steroeselective cyclization of allenic derivatives, wherein the nitrogen is part of a sulfonamide or a carbamate group, whereas the cyclization falls when the nitrogen id part of a formamide or a secondary amine. When the nitrogen is part of a free amine, stereoselectivity is lost.

The present inventors have surprisingly found that Ag-salts catalyse the stereoselective cyclization of phosphonamidic allenes. Accordingly, it is possible to prepare a compound of formula II by catalytically converting a compound of formula III

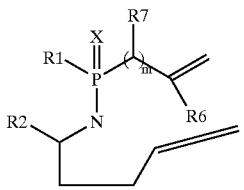

III wherein R1, R2, R6, R7, X, and m are as described above.

This Ag+ catalysed cyclization may be run under various conditions. Preferably, it is run at temperatures ranging from 0–40° C., e.g. 10–30° C. The amount of Ag+ salt used ranges from 0.05–2 equivalents, e.g. 0.5–1.5, with respect to the allene. The cyclization may run for any amount of time required to reach the transformation needed and may involve more than one addition of Ag salt. Useful Ag salts may be selected from the group consisting of $AgOCOCF_3$, $AgClO_4$, $AgOSO_2CF_3$, $AgNO_3$ and $AgBF_4$.

The invention is further illustrated by the following non-limiting examples.

EXAMPLES

The following standard abbreviations are used: DCM: Dichloro methane; THF: Tetrahydro furane; $NH_2OTMS$: O-(trimethylsilyl) hydroxylamine; DMSO: Dimethyl sulfoxide.

Drying of solvents was effected by adding oven dried molecular sieves to commercial, dry solvents. All melting points are uncorrected. Chemical shift values (δ) (in ppm) are quoted for $^{13}C$ NMR (75.6 MHz) in solvent specified, relative to internal tetramethylsilane (δ=0.00) or deuteriochloroform (δ=76.81). Mass spectra were recorded on a QUATTRO II (Micromass). The mode is indicated as EI+: electron impact, positive ions; ES+: electrospray, positive mode. Accurate masses are given together with the relative deviations from theory in brackets.

Synthesis

Benzenephosphinyl dichloride 1a was commercially available. Commercially available aryl ethers were dichlorophosphinylated (Miles, *J. Org. Chem.*, 40, 343–347, 1975) with trichlorophosphine and 0.1–0.2 molar equivalents of a Lewis acid (Aluminium chloride for diaryl ethers and Tin (IV)chloride for aryl alkyl ethers) under reflux for three days followed by distillation (Scheme 1), yielding aryldichlorophosphines 1b–f in moderate to poor yields. The phosphinyl chlorides were treated with ω-unsaturated alcohols, and the resulting phosphinates underwent Arbuzov rearrangement when heated at 130° C. either neat (allyl allyarylphosphonates 2) or in the presence of catalytic alkyl bromide: 4-bromobut-1-ene for the synthesis of butenyl arylbutenylphosphonates 3 and 5-bromopent-1-ene for the synthesis of pentenyl arylpentenylphosphonates 4.

Scheme 1

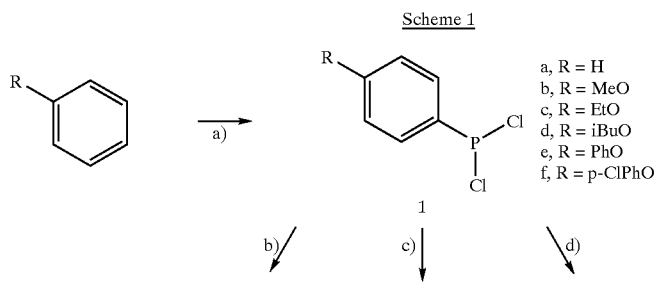

a, R = H
b, R = MeO
c, R = EtO
d, R = iBuO
e, R = PhO
f, R = p-ClPhO

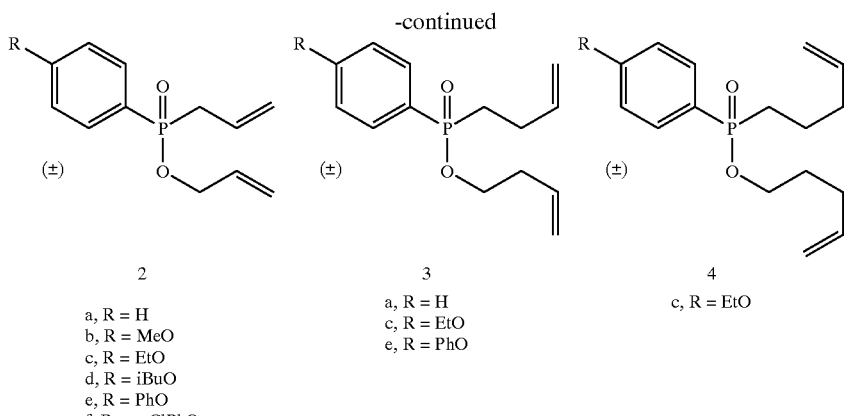

2
a, R = H
b, R = MeO
c, R = EtO
d, R = iBuO
e, R = PhO
f, R = p-ClPhO 3
a, R = H
c, R = EtO
e, R = PhO 4
c, R = EtO a): PCl$_3$/SnCl$_4$ or PCl$_3$/AlCl$_3$; b): i. Allylalcohol, pyridine, ether; ii. heat; c): i. But-3-en-1-ol, pyridine, ether ii. 4-Bromobut-1-ene, hea
d): i. Pent-4-en-1-ol, pyridine, ether ii. 5-Bromopent-1-ene, heat.

Scheme 2 b. R = MeO

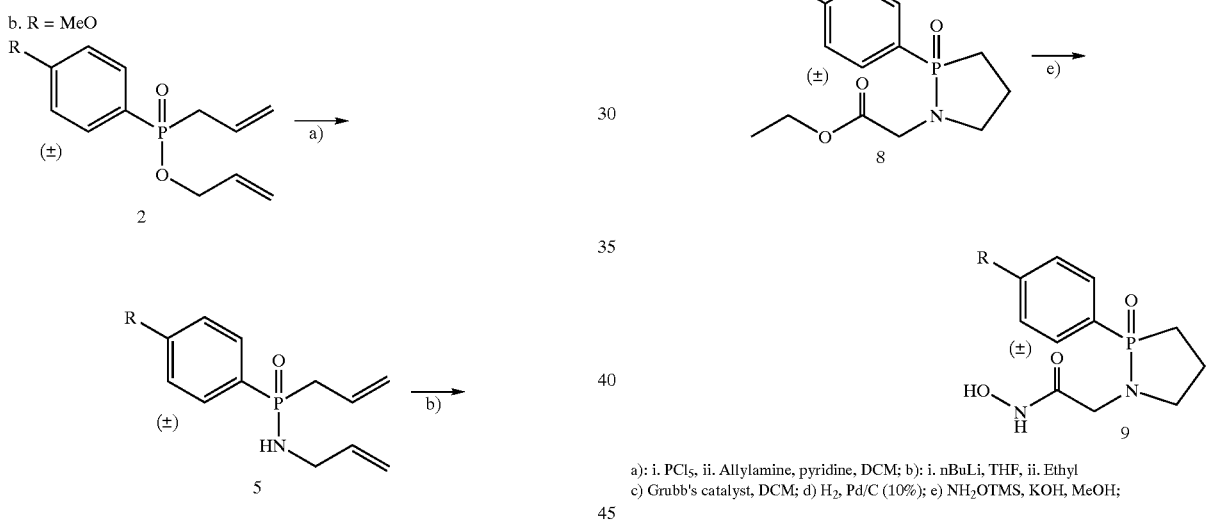

a): i. PCl$_5$, ii. Allylamine, pyridine, DCM; b): i. nBuLi, THF, ii. Ethyl
c) Grubb's catalyst, DCM; d) H$_2$, Pd/C (10%); e) NH$_2$OTMS, KOH, MeOH;

Precursors for azaphosphorolanes (5-membered rings) were prepared from phosphonate esters 2, which were converted smoothly to phosphonyl chlorides with phosphorous pentachloride in DCM (Scheme 2). Subsequent phosphonylation of allylamine afforded the phosphonamides 5, (Hetherington, Tetrahedron, 56, 2053–2060, 2000). With prolonged reaction times under strongly basic conditions, alkylation with ethyl bromoacetate was accompanied by double bond migration, and subsequent Ring Closing Metathesis neatly afforded azaphosphorolenes 7. Catalytic hydrogenation yielded the heterocycles 8, which were converted to hydroxamic acids 9 using O-trimethylsilylhydroxylamine and potassium hydroxide monohydrate in Methanol.

Scheme 3

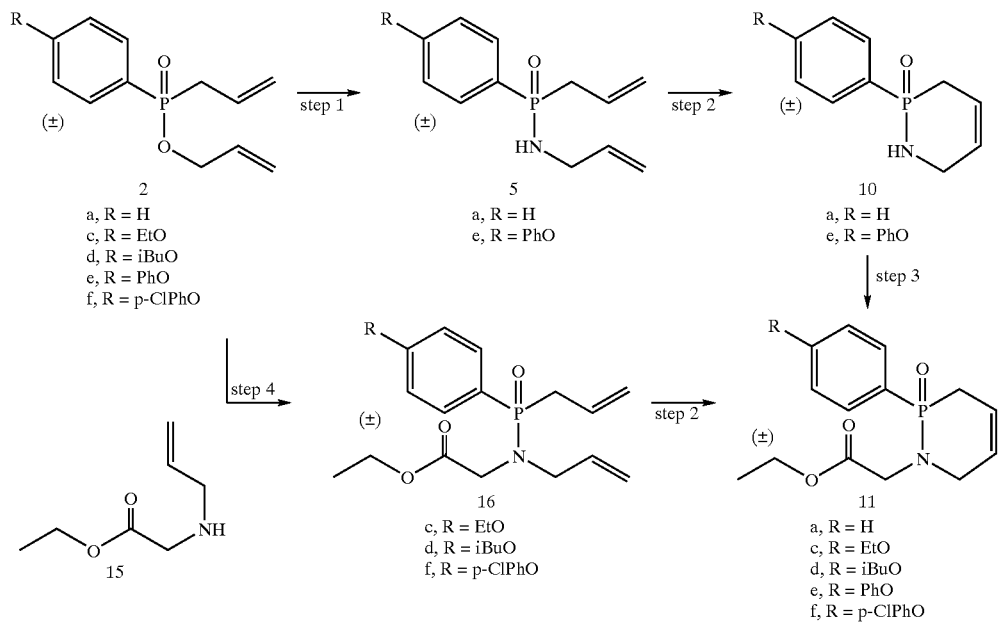

step 1) i. PCl₅, DCM, ii. Allylamine, triethylamine, DCM. step 2) Grubb's catalyst, DCM.
step 3) i. nBuLi, THF, ii. Ethyl bromoacetate; step 4) i. PCl₅, DCM, ii. 15, triethylamine, DCM.

Azaphosphorines were prepared via key intermediary esters 11 (Sheme 3). Phosphonates 2 were chlorinated with phosphorouspentachloride and phosphonylated allylamine yielding phosphonamides 5, which were cyclized with Grubb's catalyst and alkylated with ethyl bromoacetate to yield key intermediary esters, 11. Alternatively, these key intermediates were accessible by phosphonylation of N-allylglycine ethyl ester 15 with phosphonyl chlorides, as above, followed by Ring Closing Metathesis.

Scheme 4

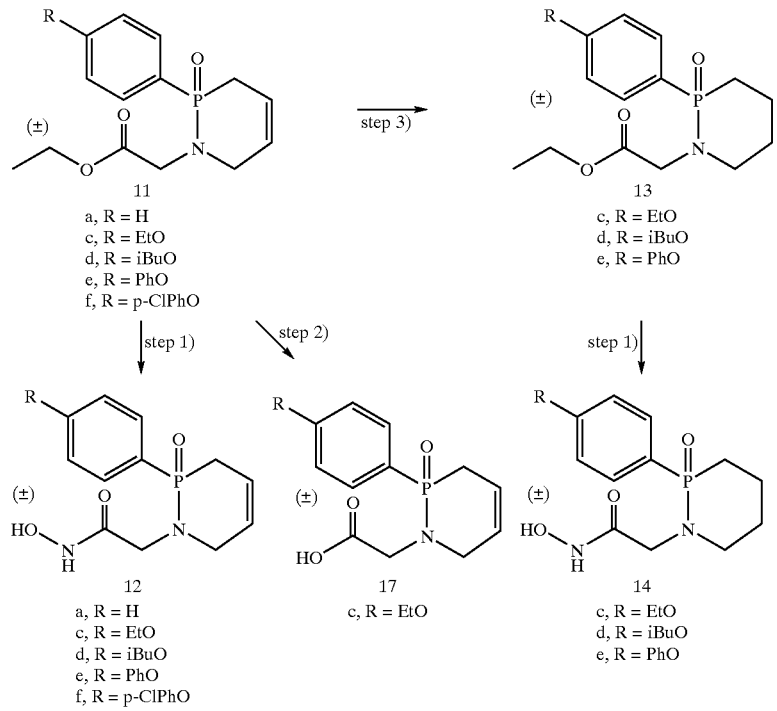

step 1) TMSONH₂, KOH, MeOH. step 2) NaOH, MeOH. step 3) H₂, Pd/C (10%).

Esters 11 then underwent hydroxylaminolysis yielding hydroxamic acids 12, or saponification, yielding carboxylic acids 17 (Scheme 4). Finally, hydrogenation and hydroxylaminolysis afforded hydroxamic acids 14 via esters 13.
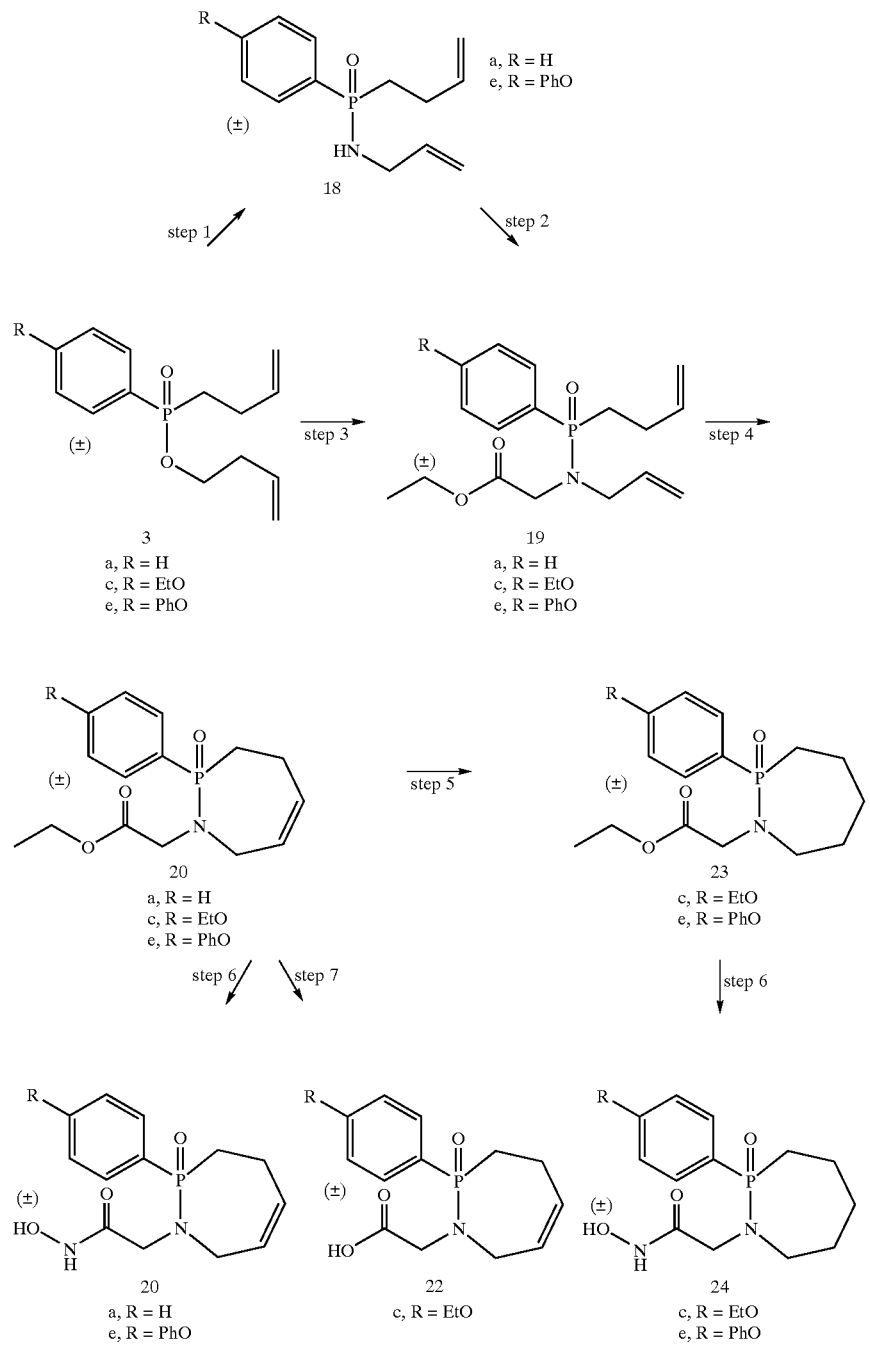

Also 7-membered heterocyclic hydroxamic acids and carboxylic acids 21, 22, and 24 were accessible from butenyl arylbutenylphosphonates 3 after amidation of allylamine as before, yielding phosphonamides 18, which were alkylated with ethyl bromoacetate to give key intermediate di-unsaturated esters, 19, (Scheme 5). Alternatively, these dienes were accessed directly by phosphonylatin N-allylglycin ethyl ester with phosphonyl chlorides obtained from phosphonates 3. Again, Ring Closing Metathesis afforded heterocyclics, 20, which were optionally hydrogenated to esters 23 prior hydroxylaminolysis or hydrolysis to yield hydroxamic acids and carboxylic acids 21, 22, and 24.

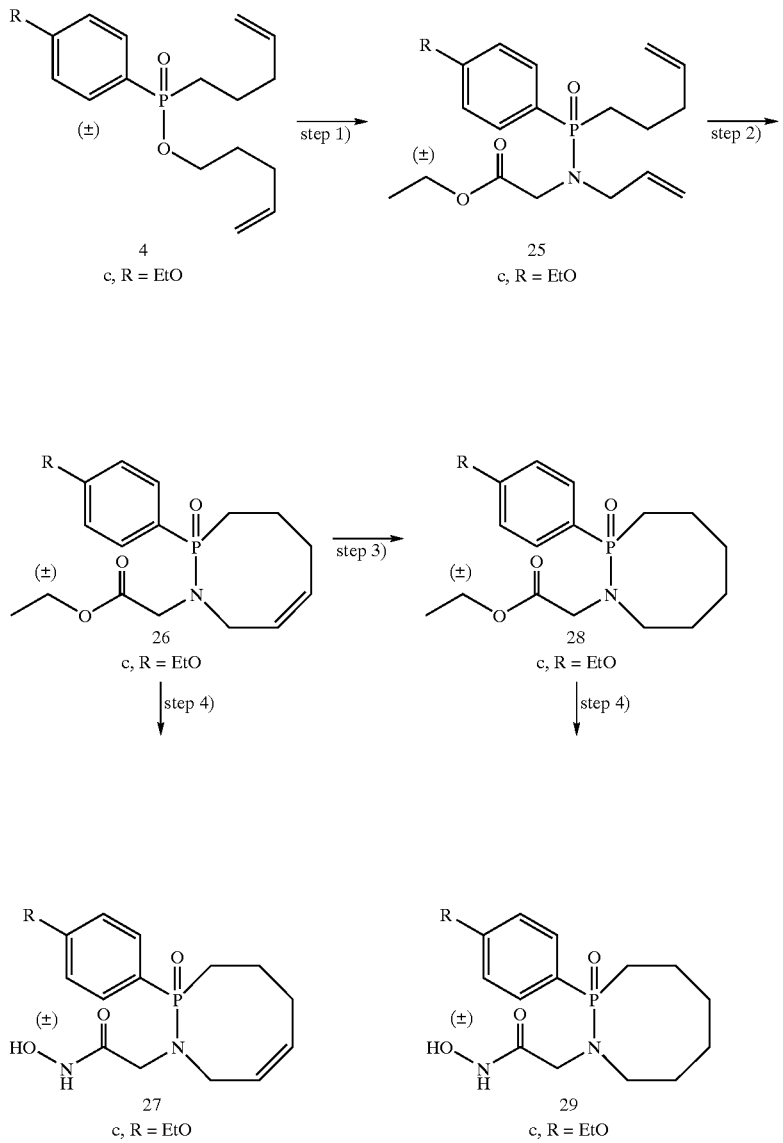

step 1) i. PCl₅, DCM, ii. 15, triethylamine, DCM. step 2) Grubb's catalyst, DCM.
step 3) H₂Pd/C (10%). step 4) TMSONH₂, KOH, MeOH.

The same sequence of events allowed the transformation of pentenyl arylpentenylphosphonates 4 into phosphonamides 25, which again smoothly cyclized to unsaturated heterocycles 26, (Scheme 6). These azaphosphorocenones were transformed to hydroxamic acids 27, or optionally hydrogenated to heterocycles 28 before hydroxylaminolysis yielding 29.

Scheme 7

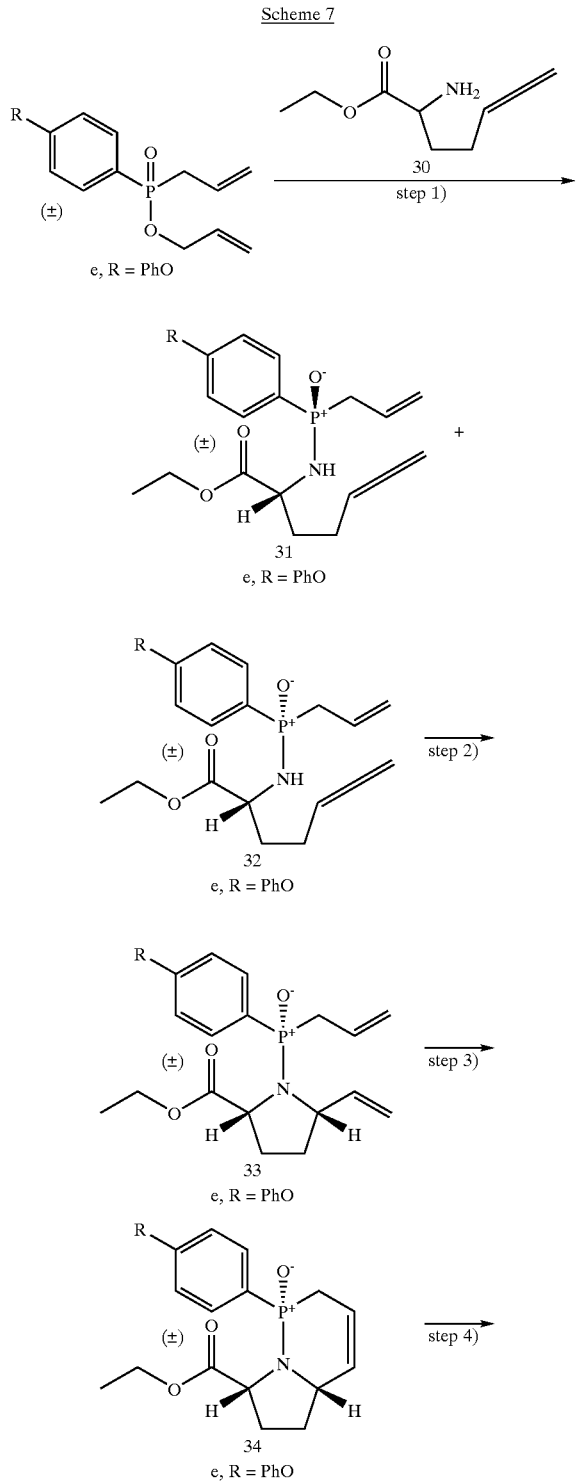

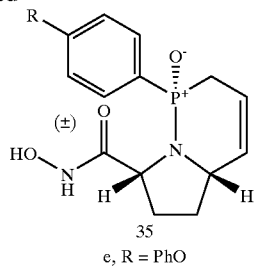

35
e, R = PhO step 1) i. PCl$_5$, DCM, ii. 30, triethylamine, DCM. step 2) AgBF$_4$, THF. step 3) Grubb's catalyst, DCM. step 4), NH$_2$OTMS, KOH, MeOH.

The bicyclic compounds with a 5- and a 6-membered ring fused were accessible as detailed in Scheme 7. The phosphonyl chloride derived from phosphonate 2 with phosphorous pentachloride, when treated with aminoester 30 (Huby, J. Chem. Soc., Perkin trans., 1, 145–155, 1991.) gave pure phosphonamides as mixtures of diastereomers 31 and 32, which were separated by chromatography. One of the isomers was carried through the following steps. Cyclization of the aminoallene to a five membered ring was effected with silver ion catalysis (For details, see preparation 33e) forming a pyrrolidine, 33, with the two pyrrolidine substituents on carbon exclusively in the cis-orientation. Ring Closing Metathesis again cyclized the diene, this time forming bicyclic 34. At this point, the stereochemistry was determined by NMR-spectroscopic methods to be that depicted for compound 34. Hydroxamic acid 35 was finally prepared by hydroxaminolysis, as before.

General Procedures:

Dichlorophosphinylation with Aluminium Chloride.

The aromatic compound was heated at reflux with trichlorophosphine (1 molar equvalent) and aluminium chloride (0.1 molar equivalent) for three days under a stream of escaping argon. Unreacted trichlorophosphine was removed by distillation at atmospheric pressure. The crude product was distilled quickly at 0.05 mmHg, and the distillate carefully redistilled at 0.05 mmHg to give a lower boiling fraction of unreacted aromatic, and the desired dichloroarylphosphine as the higher boiling product.

Dichlorophosphinylation with Tin(VI)Chloride.

The aromatic compound was heated at reflux with trichlorophosphine (1 molar equvalent) and tin(IV)chloride (0.1 molar equivalent) for three days under a stream of escaping argon. Unreacted trichlorophosphine was removed by distillation at atmospheric pressure. The crude product was distilled quickly at 0.05 mmHg, and the distillate carefully redistilled at 0.05 mmHg to give a lower boiling fraction of unreacted aromatic, and the desired dichloroarylphosphine as the higher boiling product.

Allyl/Arbuzov Sequence

The aryl-dichloro-phosphine was dissolved at 0.25M in dry diethyl ether under argon and ice cooling. Pyridine (2.2 molar equivalents) was added, followed by allyl alcohol (2.2 molar equivalents). After two hours at room temperature, the mixture was filtered under minimal exposure to air, the filter washed with more dry Diethyl ether, and the filtrate concentrated in vacuo. Solvent residues were removed in high vacuum. The residue was heated at 130° C. over night and chromatographed on silica gel in a gradient of ethyl acetate in toluene rising from 0% to 100%. Fractions containing product were identified by TLC (iodine vapour), combined, and concentrated in vacuo, yielding the pure product as an oil.

Butenyl/Arbuzov Sequence

The aryl-dichloro-phosphine was dissolved at 0.25M in dry diethyl ether under argon and ice cooling. Pyridine (2.2 molar equivalents) was added, followed by but-3-enol (2.2 molar equivalents). After two hours at room temperature, the mixture was filtered under minimal exposure to air, the filter washed with additional dry diethyl ether, and the filtrate concentrated in vacuo. Solvent residues were removed in high vacuum. 4-bromobut-1-ene (1 molar equivalent) was added, the solution heated at 120° C. over night and chromatographed on silica gel in a gradient of ethyl acetate in toluene rising from 0% to 100%. Fractions containing product were identified by TLC (iodine vapour), combined, and concentrated in vacuo, yielding the pure aryl-(but-3-enoxy)-but-3-enylphosphone as an oil.

Pentenyl/Arbuzov Sequence.

In a procedure similar to the butenyl/Arbuzov sequence, aryl-dichlorophosphine was reacted first with pent-4-enol and then 5-bromopent-1-ene to afford the pure aryl-(pent-4-enoxy)-pent-4-enylphosphone.

Amidation

The alkoxyphosphone was dissolved under argon in dry dichloromethane (to 0.5 M), and phosphorpentachloride (1.05 molar equivalents) was added. After stirring at room temperature for three hours, volatiles were removed in vacuo, and a high vacuum (0.04 mmHg) was applied for 15 minutes. The residue was redissolved under argon in dry dichloromethane (to 0.5 M), and the allylic amine (2 molar equivalents) was added, followed by triethylamine (2 molar equivalents). After three hours, the mixture was evaporated onto silica gel (1g of silica gel per 100 mg of product) and eluted with a gradient of methanol in ethyl acetate rising from 0% to 10%. Fractions containing product were identified by TLC (iodine vapour), and combined. Removal of solvents in vacuo yielded the pure product as an oil.

Ring Closing Metathesis

The diene was dissolved to 0.01M in dichloromethane, and Grubb's catalyst, benzylidene-bis-(tricyclohexylphosphine)-dichloro-ruthenium (0.02 molar equivalents), was added. When the reaction had gone to completion (within two hours), the reaction mixture was evaporated onto silica gel (1 g silica gel per 100 mg product) and eluted in a gradient of methanol in ethyl acetate rising from 0% to 10%. Fractions containing product were identified by TLC (iodine vapour), combined, and concentrated in vacuo to give the pure product as an oil.

Alkylation

To the phosphonamide suspended at 0° C. in dry THF at 0.5M was added butyl lithium (1.15 molar equivalents of a 1.6 M solution in hexanes). When all solids had dissolved, the solution was cooled to −78° C., ethyl bromoacetate (1.6 molar equivalents) was added, and the reaction mixture left to reach room temperature. The next day, aqueous work up with phosphate buffer at pH 7 and ethyl acetate followed by chromatography in a gradient of ethyl acetate in hexane rising from 0% to 10% afforded the pure product as an oil.

Hydroxaminolysis

To the ethyl ester, dissolved at 0.7M in dry methanol at 0° C., was added O-trimethylsilyl hydroxylamine (2 molar equivalents), followed by potassium hydroxide monohydrate (2 molar equivalents) dissolved at 1M in dry methanol. When TLC indicated complete conversion, aqueous work up with phosphate buffer at pH 2 and ethyl acetate, and drying with magnesium sulphate, afforded a crude product, which was evaporated onto silica gel (1 g of silica gel per 100 mg of crude product) and eluted with a gradient of methanol in chloroform rising from 0% to 15%. Fractions containing the hydroxamic acid were identified on TLC plates with ferrichloride spray, combined, and concentrated in vacuo to give the pure hydroxamic acid.

Hydrogenolysis

The cyclic olefin, 70 mg, was shaken in ethyl acetate (2 ml) with 10% palladium on carbon (30 mg) under hydrogen at 1 atm., until the calculated amount of hydrogen had been absorbed. Filtration through a pad of celite and removal of solvent yielded the corresponding saturated product in a pure state.

Hydrolysis.

The ester was dissolved in methanol (to 0.1 M) and NaOH (aqueous, 2M, 20 molar equivalents) was added at room temperature. When TLC indicated complete conversion, the solution was acidified with hydrochloric acid and extracted with ethyl acetate. The extract was dried over magnesium sulphate, stripped of solvents in vacuo, and chromatographed in a gradient of methanol in dichloromethane rising from 10% to 50%. Fractions containing product were identified with TLC (iodine vapour), combined, and reduced in vacuo to the pure carboxylic acid.

Individual Preparations:

The following compounds were prepared employing the general procedures detailed above:

2a (±) Allyl Allylphenylphosphonate.

Prepared from 1a by the allyl/Arbuzov sequence as an oil.

3a (±) But-3-enyl But-3-enylphenylphosphonate.

Prepared from dichloro-phenylphosphine by the butenyl/Arbuzov procedure as an oil.

18a (±) Allyl But-3-enylphenylphosphonamide.

Prepared by amidation of 3a by allylamine as an oil.

19a (±) Allyl (ethoxycarbonyl)methyl But-3-enylphenylphosphonamide.

Prepared by alkylation of 18a with ethyl bromoacetate.

20a (±)-Ethyl 2-oxo-2-phenyl-azaphosphorep-5-ene-1-acetate.

Prepared by Ring Closing Metathesis of 19a as an oil.

21a, Example 3.

(±)-N-hydroxy-2-oxo-2-phenyl-azaphosphorep-5-ene-1-acetamide.

Prepared by hydroxylaminolysis of 20a as an oil. $^{13}$C NMR(DMSO): 166.6, 133.3, 131.5, 131.2, 130.9, 128.4, 127.6, 46.0, 44.0, 26.4, 21.5

1b

Dichloro-(4-methoxyphenyl)phosphine.

Prepared from anisole by dichlorophosphinylation with tin(IV)chloride as an oil.

2b

Allyl (±)-propenyl-(4-methoxyphenyl)phosphonate.

Prepared from 1b by the allyl/Arbuzov sequence as an oil.

5b

Allyl (±)-allyl-(4-methoxyphenyl)phosphonamide.

Prepared from 2b by amidation with allylamine as an oil.

6b

Allyl Ethoxycarbonylmethyl (±)-propenyl-(4-methoxyphenyl)phosphonamide.

Prepared from 5b by alkylation with ethyl bromoacetate as an oil, resulting from double bond isomerisation prior to work up.

7b

Ethyl (±)-2-(4-Methoxyphenyl)-2-oxo-azaphosphorol-3-ene-1-acetate.

Prepared from 6b by ring closing metathesis in as an oil.

8b

Ethyl (±)-2-(4-methoxyphenyl)-2-oxo-azaphosphorolane-1-acetate.

Prepared from 7b by hydrogenation as an oil.

9b, Example 7.

(±)-N-hydroxy-2-(4-methoxyphenyl)-2-oxo-azaphosphorolane-1-acetamide.

Prepared from 8b by hydroxylaminolysis as an oil. $^{13}$C NMR (DMSO): 165.9, 161.9, 133.8, 123.4, 114.0, 55.2, 49.5, 45.0, 26.7, 20.6

1c

Dichloro-(4-ethoxyphenyl)phosphine.

Prepared from fenethole by dichlorophosphinylation with tin(IV) chloride as an oil collected at 70–8° C./0.05 mmHg.

2c (±) Allyl Allyl-(4-ethoxyphenyl)-phosphonate.

Prepared from 1c by the allyl/Arbuzov sequence as an oil.

16c (±) Allyl Ethoxycarbonylmethyl Allyl-(4-ethoxyphenyl)-phosphonamide.

Prepared from 2c by amidation with N-allyl-glycine ethyl ester as an oil.

Ethyl(±) 2-(4-ethoxyphenyl)-2-oxo-azaphosphorin-4-ene-1-acetate

Prepared from 16c by ring closing metathesis as an oil.

12c, Example 11.

(±)-N-hydroxy-2-(4-ethoxyphenyl)-2-oxo-azaphosphorin-4-ene-1-acetamide.

Prepared from 11c by hydroxaminolysis as an oil. ES+: M+=311,1146 (4.8 ppm). $^{13}$C NMR (DMSO): 165.6, 161.0, 132.7, 126.3, 123.9, 119.8, 114.3, 63.2, 50.1, 47.3, 27.1, 14.4

17c, Example 12.

(±)-2-(4-Ethoxyphenyl)-2-oxo-azaphosphorin-4-ene-1-acetic acid.

Prepared from 11c by hydrolysis as an oil. ES+: M+=296, 1058 (2.0 ppm). $^{13}$C NMR (DMSO): 161.3, 133.8, 126.9, 122.0, 118.7, 114.3, 63.2, 52.0, 49.2, 27.0, 14.4

13c

Ethyl (±)2-(4-ethoxyphenyl)-2-oxo-azaphosphorinane-1-acetate.

Prepared from 11c by hydrogenation as an oil.

14c, Example 13.

(±)-N-hydroxy-2-(4-ethoxyphenyl)-2-oxo-azaphosphorinane-1-acetamide.

Prepared from 13c by hydroxylaminolysis as an oil. EI+: M+=312,1230 (2.9 ppm). $^{13}$C NMR (DMSO): 165.5, 161.3, 133.7, 122.3, 114.5, 63.2, 49.2, 48.6, 27.3, 25.7, 20.4, 14.4

3c (±) But-3-enyl But-3-enyl-(4-ethoxyphenyl)phosphonate.

Prepared from 1c by the allyl/Arbuzov sequence as an oil.

19c (±) Allyl Ethoxycarbonylmethyl But-3-enyl-(4-ethoxyphenyl)phosphonamide.

Prepared from 3c by amidation of N-allyl-glycine ethyl ester yield as an oil.

20c

Ethyl (±)-2-(4-ethoxyphenyl)-2-oxo-azaphosphorep-5-ene-1-acetate.

Prepared from 19c by Ring Closing Metathesis as an oil.

22c, Example 14.

(±)-2-(4-Ethoxyphenyl)-2-oxo-azaphosphorep-5-ene-1-acetic Acid.

Prepared from 20c by hydrolysis as an oil. $^{13}$C NMR (DMSO) 172.3, 161.0, 132.9, 131.1, 127.8, 124.1, 114.3, 63.2, 47.1, 44.1, 26.8, 21.4, 14.4

23c

Ethyl (±)-2-(4-ethoxyphenyl)-2-oxo-azaphosphorepane-1-acetate.

Prepared from 20c by hydrogenation as an oil.

24c, Example 16.

(±)-N-hydroxy-2-(4-ethoxyphenyl)-2-oxo-azaphosphorepane-1-acetamide.

Prepared from 23c by hydroxylaminolysis as an oil. $^{13}$C NMR (DMSO) 166.8, 161.0, 133.2, 124.5, 114.3, 63.2, 48.9, 48.1, 30.2, 29.4, 28.8, 20.4, 14.5

4c (±) Pent-4-enyl (4-ethoxyphenyl)pent-4-enylphosphonate.

Prepared from 1c by the pentenyl/Arbuzov sequence.

25c (±)-Allyl Ethoxycarbonylmethyl (4-ethoxyphenyl)pent-4-enylphosphonamide.

Prepared from 4c by amidation with N-allyl-glycine ethyl ester as an oil.

26c

Ethyl (±)-2-(4-ethoxyphenyl)-2-oxo-azaphosphoroc-6-ene-1-acetate.

Prepared from 25c by ring closing metathesis as an oil.

27c, Example 9.

(±)-N-hydroxy-2-(4-ethoxyphenyl)-2-oxo-azaphosphoroc-6-ene-1-acetamide.

Prepared from 26c by hydroxylaminolysis as an oil. ES+: M+=339,1465 (2.6 ppm). $^{13}$C NMR (DMSO): 166.6, 160.8, 132.6, 128.8, 128.7, 125.2, 114.1, 63.1, 46.1, 45.7, 24.9, 23.6, 21.3, 14.4

28c

Ethyl (±)-2-(4-ethoxyphenyl)-2-oxo-azaphosphorocane-1-acetate.

Prepared from 26c by hydrogenation as an oil.

29c, Example 10.

(±)-N-hydroxy-2-(4-ethoxyphenyl)-2-oxo-azaphosphorocane-1-acetamide.

Prepared from 28c by hydroxylaminolysis as an oil. ES+: M+=341,1617 (3.8 ppm). $^{13}$C NMR (DMSO): 166.7, 160.7, 132.9, 125.4, 114.1, 63.1, 45.3, 44.7, 27.3, 26.0, 25.5, 23.1, 22.1, 14.5

1d

Dichloro-(4-(2-methylpropoxy)-phenyl)phosphine.

Prepared form phenyl isobutyl ether by dichlorophosphinylation with Tin(IV) Chloride as an oil.

2d
Allyl Allyl-(4-(2-methylpropoxy)-phenyl)phosphonate.
Prepared from 1d by the allyl/Arbuzov sequence as an oil.
16d
Allyl Ethoxycarbonylmethylallyl-(4-(2-methylpropoxy)-phenyl)phosphonamide.
Prepared from 2d by amidation of N-allyl-glycine ethyl ester as an oil.
11d
Ethyl (±)-2-(4-(2-methylpropoxy)-phenyl)-2-oxo-azaphosphorin-4-ene-1-acetate.
Prepared from 16d by ring closing metathesis as an oil.
12d, Example 15.
(±)-N-hydroxy-2-(4-(2-methylpropoxy)-phenyl)-2-oxo-azaphosphorin-4-ene-5-acetamide.
Prepared from 11d by hydroxaminolysis as an oil. $^{13}$C NMR (DMSO) 165.6, 161.3, 132.8, 126.3, 123.8, 119.7, 114.4, 73.7, 50.1, 47.3, 27.6, 27.1, 18.9
13d
Ethyl (±) 2-(4-(2-methylpropoxy)-phenyl)-2-oxo-azaphosphorinane-1-acetate.
Prepared from 11d by hydrogenation as an oil.
14d, Example 17.
(±)-N-hydroxy-2-(4-(2-methylpropoxy)-phenyl)-2-oxo-azaphosphorinane-1-acetamide.
Prepared from 13d by hydroxylaminolysis as an oil. $^{13}$C NMR (DMSO) 165.5, 161.6, 133.7, 122.3, 114.5, 73.7, 49.3, 48.6, 27.6, 27.3, 25.7, 20.4, 18.9.
1e
Dichloro-(4-phenoxyphenyl)phosphine.
Prepared from phenyl ether by dichlorophosphinylation with aluminium chloride as an oil distilling at 150° C./0.05 mmHg (Kugelrohr oven).
2e
(±)-Allyl Allyl(phenoxyphenyl)phosphonate
Prepared from 1e by the allyl/Arbuzov sequence as an oil.
5e
(±)-Allyl Allyl(phenoxyphenyl)phosphonamide.
Prepared by amidation of 2e with allylamine as an oil.
10e
(±)-2-oxo-2-(4-phenoxyphenyl)-azaphosphorin-4-ene.
Prepared by ring closing metathesis of 5e.
11e
(±)-Ethyl 2-oxo-2-(4-phenoxyphenyl)-azaphosphorin-4-ene-1-acetate.
Prepared by alkylation of 10e as an oil.
12e, Example 1.
(±)-N-hydroxy-2-oxo-2-(4-phenoxyphenyl)-azaphosphorin-4-ene-1-acetamide.
Prepared by hydroxaminolysis of 11e as an oil. $^{13}$C NMR (CD3CN): 167.5, 162.1, 156.6, 134.5, 131.2, 127.6, 126.6, 125.7, 121.0, 120.4, 118.7, 51.5, 49.7, 28.0
13e
(±)-Ethyl 2-oxo-2-(4-phenoxyphenyl)-azaphosphorinane-1-acetate.
Prepared by hydrogenation of 11e in practically quantitative yield.
14e, Example 2.
(±)-N-hydroxy-2-oxo-2-(4-phenoxyphenyl)-azaphosphorinane-1-acetamide.
Prepared by hydroxylaminolysis of 13e as an oil. $^{13}$C NMR (CD3CN): 167.3, 162.2, 156.4, 135.0, 131.0, 125.5, 125.3, 120.8, 118.6, 51.7, 50.2, 28.3, 26.8, 21.1

3e
(±) But-3-enyl But-3-enyl(4-phenoxyphenyl)phosphonate.
Prepared by the butenyl/Arbuzov sequence from 1e as an oil.
18e
(±) Allyl But-3-enyl(4-phenoxyphenyl)phosphonamide.
Prepared from 3e by amidation with allylamine as an oil.
19e
(±) Allyl (Ethoxycarbonyl)methyl But-3-enyl(4-phenoxyphenyl)phosphonamide.
Prepared from 18e by alkylation with ethyl bromoacetate as an oil.
20e
Ethyl (±)-2-oxo-2-(4-phenoxyphenyl)-azaphosphorep-5-ene-1-acetate.
Prepared from 19e by Ring Closing Metathesis as an oil.
21e, Example 4.
(±)-N-hydroxy-2-oxo-2-(4-phenoxyphenyl)-azaphosphorep-5-ene-1-acetamide.
Prepared from 20e by hydroxylaminolysis as an oil. $^{13}$C NMR(DMSO): 166.5, 159.8, 155.2, 133.3, 131.1, 130.2, 127.6, 127.2, 124.4, 119.6, 117.4, 46.2, 44.0, 26.5, 21.5
23e
(±)-2-oxo-2-(4-phenoxyphenyl)-azaphosphorepane-1-acetate.
Prepared from 20e by hydrogenation in quantitative yield as an oil.
24e, Example 5.
(±)-N-hydroxy-2-oxo-2-(4-phenoxyphenyl)-azaphosphorepane-1-acetamide.
Prepared from 23e by hydroxaminolysis as an oil. MS, accurate mass, M+=374,1400 (1.1 ppm). $^{13}$C NMR (DMSO): 166.7, 159.7, 155.2, 133.5, 130.2, 127.8, 124.3, 119.7, 117.3, 48.8, 47.8, 30.0, 29.3, 28.7, 20.4
32e
(±) (1R*)-ethoxycarbonylhexa-4,5-dienyl (S*)-allyl-(4-phenoxyphenyl)-phosphonamide.
Prepared by amidation of 2e with Ethyl (±)-2-amino-hepta-5,6-dienoate (Huby, J. Chem. Soc., Perkin trans., I, 145–155, 1991.). The mixture of stereoisomers were separated by chromatography. The slower isomer 32e was isolated as an oil.
33e
Ethyl (±)-[5R*,2S*]-1-((R*)-allyl(phenoxyphenyl) phosphonyl)-5-ethenyl-pyrrolidine-2-carboxylate.
Prepared from 32e as follows: the allene, 382 mg (0.9 mmol) was dissolved in dichloromethane at 0.1M and 1 equivalent of silver(I)tetrafluoroborate was added. After 24 hours, another equivalent of silver(I)tetrafluoroborate was added, and after another 24 hours, the mixture was worked up: The mixture was diluted with dichloromethane, 25 ml, and aqueous saturated sodium chloride solution, 50 ml, and filtered. The filtrate was extracted with dichloromethane, 25 ml, and the organic phases combined, dried over magnesium sulphate, and freed of solvent in vacuo, leaving an oily residue, which was purified by chromatography in a gradient from 20% petroleum ether in ethyl acetate to 5% methanol in ethyl acetate yielding 191 mg (50%) of 33e as an oil.
34e
Ethyl (±)-(2R*,6R*,9S*)-2-oxo-2-(4-phenoxyphenyl)-1,2-azaphosphabicyclo[4.3.0]non-4-ene-9-carboxylate.
Prepared from 33e by ring closing metathesis as an oil.
35e, Example 8.
(±)-(2 R*, 6R*, 9S*)-N-hydroxy-2-oxo-2-(4-phenoxyphenyl)-1,2-azaphosphabicyclo[4.3.0]non-4-ene-9-carboxamide.

Prepared from 34e by hydroxaminolysis as an oil. MS, accurate mass, M+=384,1251 (3.1 ppm). $^{13}$C NMR (DMSO): 170.3, 159.7, 155.2, 131.9, 130.3, 130.2, 127.8, 124.4, 120.7, 119.6, 117.5, 61.0, 57.5, 31.1, 30.4, 26.5

1f

Dichloro-(4-(4-chlorophenoxy)-phenyl)-phosphine. Prepared by dichlorophosphinylation with aluminium chloride of 4-chlorophenyl phenyl ether as an oil of b.p.: 125–35° C./0.05 mmHg.

2f (±) Allyl Allyl(4-(4-chlorophenoxy)phenyl)phosphonate.

Prepared from 1f by the allyl/Arbuzov sequence as an oil.

16f (±) Allyl (Ethoxycarbonyl)methyl Allyl(4-(4-chlorophenoxy)phenyl)phosphonamide.

Prepared from 2f by amidation with N-allyl-glycine ethyl ester as an oil.

11f (±)-2-(4-(4-chlorophenoxy)-phenyl-2-oxo-azaphosphorin-4-ene-1-acetate.

Prepared from 16f by Ring Cosing Metathesis as an oil.

12f Example 6.

(±)-N-hydroxy-2-(4-(4-chlorophenoxy)-phenyl-2-oxo-azaphosphorin-4-ene-1-acetamide.

Prepared from 11f by hydroxaminolysis in the crystalline state after recrystallization from methanol/ethyl acetate. $^{13}$C NMR (DMSO): 165.5, 159.3, 154.2, 133.1, 130.0, 128.2, 127.8, 126.4, 121.4, 119.7, 117.6, 50.2, 47.0, 27.0

Test for MMP Inhibitory Effects

The assay measures the effect of the tested compounds on the proteolytic activity of metalloproteases by assessing the cleavage of a fluorogenic substrate. In the uncleaved substrate the fluoresensce is quenched intramolecularly, however, cleavage of the substrate relieves the quenching yielding fluorescent peptides [Bickett, *Anal. Biochem*, 212, 58–64, 1993; Knight, *FEBS Lett.*, 296, 263–266, 1992].

The compounds were tested for inhibitory effects towards MMP-1 and MMP-9 (Chemicon International, CA, USA) and MMP-2 (Biogenesis Ltd, UK). Substrate for MMP-1 was M-2055 (Dnp-Pro-β-cyclohexyl-Ala-Gly-Cys(Me)-His-Ala-Lys(N-Me-Abz)-NH$_2$), which is a synthetic peptide-like structure, obtained from Bachem AG, Schwitzerland. Substrate for MMP-2 and MMP-9 was fluorescein-conjugated gelatin obtained from Molecular Probes Inc., OR, USA.

The enzymes were activated with phenyl mercuric acetate, and incubated with the appropriate substrate and different levels of the compound to be tested. The exitation/emission wavelengths were 350/450 and 485/530 for M-2055 and gelatine, respectively.

The molar concentration of the test compounds resulting in 50% inhibition of the enzymatic activity (IC$_{50}$) was calculated from the dose-response curve. For convenience, the results are reported as pIC$_{50}$, i.e. –log(IC$_{50}$).

The results are shown in Table 1 below
pIC$_{50}$ for cyclo azaphospha hydrocarbons

|           | MMP-1 | MMP-2 | MMP-9 |
|-----------|-------|-------|-------|
| Example 1 | 5.6   | 8.3   | 9.0   |
| Example 4 | 5.1   | 8.1   | 8.2   |
| Example 5 | 5.2   | 8.3   | 8.5   |
| Example 6 | 5.3   | 8.4   | 9.1   |

As shown in the table, cyclo phospha hydrocarbons exhibit strong inhibitory effect towards MMP.

What is claimed is:

1. A compound of the general formula I

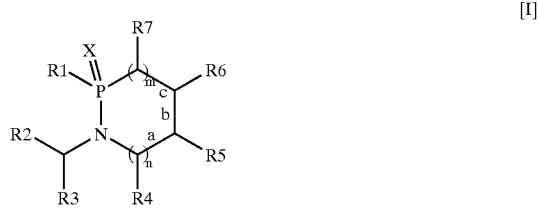

[I]

wherein bonds denoted a, b and c independently represents single or double bonds;

m and n are independently 0, 1, 2 or 3, provided that m and n are not both 0;

X is S or O;

R$_1$ is

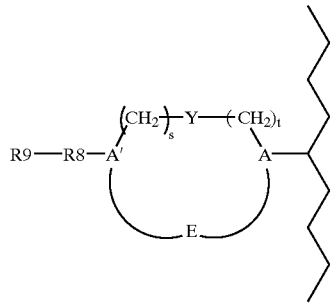

wherein E, when present represents a bond, methylene or ethylene optionally substituted with halogen, hydroxy, cyano, nitro, C$_{1-4}$ alkyl, haloalkyl, hydroxyalkyl, alkoxy or alkylcarbonyl;

s and t are independently 0, 1, 2 or 3;

A and A' independently represent a bond, or a saturated or unsaturated, optionally substituted cyclic or heterocyclic hydrocarbon di- or triradical;

Y represents a bond, O, S, C(O)NR$_{10}$, NR$_{10}$C(O) or NR$_{10}$, wherein R$_{10}$ is hydrogen, hydroxy, branched or straight, saturated or unsaturated hydrocarbon diradical, optionally substituted with halogen, nitro, cyano, hydroxyl, alkoxy, alkylcarbonyl or alkylamino;

R$_8$ represents a bond, hydrogen, alkan or alken diradical, one or more ether diradicals (R'—O—R") or amine diradicals (R'—N—R"), wherein R' and R" independently represent alkyl or alkenyl with a C-content from 0 to 3;

R$_9$ represents hydrogen, hydroxy, halogen, cyano, nitro, branched or straight, saturated or unsaturated hydrocarbon radical, optionally substituted with halogen, cyano, hydroxyl, alkoxy, alkylcarbonyl or alkylamino; $NR_{11}R_{12}$, $C(O)NR_{11}R_{12}$, $C(O)R_{11}R_{12}$, $CO(O)R_{11}R_{12}$, $S(O)_2R_{11}$, wherein each $R_{11}$ and $R_{12}$ independently represent hydrogen, halogen, a branched or straight, saturated or unsaturated hydrocarbon radical, optionally substituted with halogen, cyano, hydroxyl, alkoxy, alkylcarbonyl or alkylamino;

$R_2$ represents hydroxamic acid, carboxylic acid, phosphonic acid or a mercaptomethyl group;

$R_3$ and $R_4$ each independently represent hydrogen, halogen, cyano, hydroxy, nitro, branched or straight, saturated or unsaturated alkane or alkene radical, optionally substituted with halogen, cyano, nitro, hydroxyl, alkoxy, alkylcarbonyl or alkylamino; or $R_3$ and $R_4$ together with the carbon atoms to which they are attached and the connecting nitrogen atom form a hetero cyclic ring;

each $R_5$, $R_6$, and $R_7$ independently represents hydrogen, hydroxy, nitro, cyano, halogen, branched or straight, saturated or unsaturated hydrocarbon radical, optionally substituted with halogen, cyano, nitro, hydroxyl, alkoxy, alkylcarbonyl or alkylamino; or $R_4$ and $R_5$, $R_5$ and $R_6$ or $R_6$ and $R_7$, together with the carbon atom to which they are attached form a saturated or unsaturated, optionally substituted cyclic or heterocyclic ring;

and pharmaceutically acceptable salts thereof.

2. A compound according to claim 1 wherein X is O.

3. A compound according to claim 1 wherein a and c are both single bonds; b is a double bond and $R_4$ and $R_7$ are independently either hydrogen or methyl.

4. A compound according to claim 1 wherein E is absent; s and t are both 0 and Y is O in the para position on A; a being phenyl.

5. A compound according to claim 1 wherein $R_2$ is hydroxamic acid.

6. A compound according to claim 1 selected from the group consisting of (±)-N-hydroxy-2-oxo-2-(4-phenoxyphenyl)-azaphosphorin-4-ene-1-acetamide;

(±)-N-hydroxy-2-oxo-2-(4-phenoxyphenyl)-azaphosphorinane-1-acetamide;

(±)-N-hydroxy-2-oxo-2-phenyl-azaphosphorep-5-ene-1-acetamide;

(±)-N-hydroxy-2-oxo-2-(4-phenoxyphenyl)-azaphosphorep-5-ene-1-acetamide;

(±)-N-hydroxy-2-oxo-2-(4-phenoxyphenyl)-azaphosphorepane-1-acetamide;

(±)-N-hydroxy-2-(4-(4-chlorophenoxy)-phenyl-2-oxo-azaphosphorin-4-ene-1-acetamide;

(±)-N-hydroxy-2-(4-Methoxyphenyl)-2-oxo-azaphosphorolane-1-acetamide;

(±)-(R*,R*,S*)-N-hydroxy-2-oxo-2-(4-phenoxyphenyl)-1,2-azaphosphabicyclo[4.3.0] non-4-ene-9-carboxamide;

(±)-N-hydroxy-2-(4-Ethoxyphenyl)-2-oxo-azaphosphoroc-6-ene-1-acetamide;

(±)-N-hydroxy-2-(4-Ethoxyphenyl)-2-oxo-azaphosphorin-4-ene-1-acetamide;

(±)-2-(4-Ethoxyphenyl)-2-oxo-azaphosphorin-4-ene-1-acetic acid;

(±)-N-hydroxy-2-(4-Ethoxyphenyl)-2-oxo-azaphosphorinane-1-acetamide;

(±)-N-hydroxy-2-(4-Ethoxyphenyl)-2-oxo-azaphosphorocane-1-acetamide;

(±)-2-(4-Ethoxyphenyl)-2-oxo-azaphosphorep-5-ene-1-acetic acid;

(±)-N-hydroxy-2-(4-(2-methylpropoxy)-phenyl)-2-oxo-azaphosphorin-4-ene-1-acetamide; (±)-N-hydroxy-2-(4-Ethoxyphenyl)-2-oxo-azaphosphorepane-1-acetamide; and (±)-N-hydroxy-2-(4-(2-methylpropoxy)-phenyl)-2-oxo-azaphosphorinane-1-acetamide.

7. A pharmaceutical composition comprising a compound of formula I according to any one of claims 1–6 or a pharmaceutically acceptable salt thereof together with a pharmaceutically acceptable excipient.

8. A method for the treatment or prophylaxis of diseases or conditions involving tissue breakdown, inflammation, proliferative disorder, neuroinflammatory disorder, angiogenesis dependent diseases comprising administering to a patient in need thereof an effective amount of a compound according to any one of the claims 1–6.

9. A method according to claim 8 wherein the disease or condition is rheumatoid arthritis, osteoarthritis, osteopenias, osteoporosis, periodontitis, gingivitis, corneal epidermal or gastric ulceration, skin aging, tumour metastasis, tumour invasion, tumour growth, multiple sclerosis, arthritic conditions, solid tumour growth, psoriasis, proliferative retinopathies, neovascular glaucoma, ocular tumours, angiofibromas, hemangiomas, arthritis, asthma, septic shock, fever, cardiovascular effects, haemorrage, coagulation, acute phase reponse and apoptosis.

* * * * *